United States Patent
Sharma et al.

(10) Patent No.: US 11,998,335 B2
(45) Date of Patent: Jun. 4, 2024

(54) SYSTEMS AND METHODS OF CAPTURING EYE-GAZE DATA

(71) Applicant: Microsoft Technology Licensing, LLC, Redmond, WA (US)

(72) Inventors: Jatin Sharma, Sammamish, WA (US); Jonathan T. Campbell, Redmond, WA (US); Jay C. Beavers, Duvall, WA (US); Peter John Ansell, Renton, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 469 days.

(21) Appl. No.: 17/234,568

(22) Filed: Apr. 19, 2021

(65) Prior Publication Data

US 2022/0330863 A1 Oct. 20, 2022

(51) Int. Cl.
*A61B 5/16* (2006.01)
*A61B 5/00* (2006.01)

(52) U.S. Cl.
CPC ............ *A61B 5/163* (2017.08); *A61B 5/7267* (2013.01); *A61B 5/7435* (2013.01)

(58) Field of Classification Search
CPC ....................................................... G06F 3/013
See application file for complete search history.

(56) References Cited

U.S. PATENT DOCUMENTS

| 6,152,563 | A | 11/2000 | Hutchinson et al. |
| 10,884,494 | B1 | 1/2021 | Lagies et al. |
| 11,301,969 | B1 | 4/2022 | Khan et al. |
| 11,619,993 | B2 | 4/2023 | Sharma et al. |
| 2012/0230547 | A1 | 9/2012 | Durnell et al. |
| 2017/0119298 | A1 | 5/2017 | Cheung |
| 2017/0344840 | A1* | 11/2017 | Brown ................. G06V 40/197 |
| 2017/0364149 | A1 | 12/2017 | Lu et al. |

(Continued)

FOREIGN PATENT DOCUMENTS

| CN | 110705504 A | 1/2020 |
| CN | 112132755 A | 12/2020 |
| CN | 112148112 A | 12/2020 |

OTHER PUBLICATIONS

Mounica, Low Cost Eye Gaze Tracker Using Web Camera (2019).*

(Continued)

*Primary Examiner* — Di Xiao

(57) ABSTRACT

Systems and methods are provided for collecting eye-gaze data for training an eye-gaze prediction model. The collecting includes selecting a scan path that passes through a series of regions of a grid on a screen of a computing device, moving a symbol as an eye-gaze target along the scan path, and receiving facial images at eye-gaze points. The eye-gaze points are uniformly distributed within the respective regions. Areas of the regions that are adjacent to edges and corners of the screen are smaller than other regions. The difference in areas shifts centers of the regions toward the edges, density of data closer to the edges. The scan path passes through locations in proximity to the edges and corners of the screen for capturing more eye-gaze points in (Continued)

the proximity. The methods interactively enhance variations of facial images by displaying instructions to the user to make specific actions associated with the face.

17 Claims, 11 Drawing Sheets

(56) References Cited

U.S. PATENT DOCUMENTS

| | | | |
|---|---|---|---|
| 2020/0050265 A1 | 2/2020 | Krishnakumar | |
| 2020/0097076 A1 | 3/2020 | Alcaide et al. | |
| 2020/0121179 A1 | 4/2020 | Prusky et al. | |
| 2020/0159315 A1* | 5/2020 | Myers | G06F 9/453 |
| 2020/0169693 A1 | 5/2020 | Silveira et al. | |
| 2020/0202561 A1 | 6/2020 | Liu et al. | |
| 2020/0218345 A1 | 7/2020 | Liu et al. | |
| 2020/0393896 A1 | 12/2020 | Li et al. | |
| 2021/0020159 A1* | 1/2021 | Tran | G10L 13/00 |
| 2021/0056293 A1 | 2/2021 | Mn et al. | |
| 2021/0072824 A1* | 3/2021 | Wiemer | G06V 40/172 |
| 2021/0374994 A1* | 12/2021 | Lu | G01S 5/16 |
| 2022/0114327 A1* | 4/2022 | Faaborg | G06F 18/214 |
| 2022/0334637 A1 | 10/2022 | Sharma et al. | |
| 2023/0195224 A1 | 6/2023 | Sharma et al. | |

OTHER PUBLICATIONS

"Head Pose Estimation", Retrieved from: https://www.youtube.com/watch?v=NlgKWr4OxoE&t=8s, Sep. 26, 2016, 3 Pages.

Mallick, Satya, "Head Pose Estimation using OpenCV and Dlib", Retrieved from: https://learnopencv.com/head-pose-estimation-using-opencv-and-dlib/, Sep. 26, 2016, 9 Pages.

Sharma, et al., "Towards Hardware-Agnostic Gaze-Trackers", In Journal of Computing Research Repository, Oct. 11, 2020, 9 Pages.

"Notice of Allowance Issued in U.S. Appl. No. 17/234,493", dated Nov. 23, 2022, 7 Pages.

"Non Final Office Action Issued in U.S. Appl. No. 17/234,493", dated Aug. 4, 2022, 12 Pages.

Akinyelu, et al., "Convolutional Neural Network-Based Methods for Eye Gaze Estimation: A Survey", In the Journal of IEEE Access, vol. 8, Jul. 31, 2020, pp. 142581-142605.

Gudi, et al., "Efficiency in Real-time Webcam Gaze Tracking", In the Repository of arXiv:2009.01270v1, Sep. 2, 2020, 15 Pages.

"International Search Report and Written Opinion Issued in PCT Application No. PCT/US22/023187", dated Jul. 19, 2022, 11 Pages.

"International Search Report and Written Opinion Issued in PCT Application No. PCT/US22/024250", dated Aug. 1, 2022, 12 Pages.

"Non Final Office Action Issued in U.S. Appl. No. 18/113,222", dated Jul. 31, 2023, 10 Pages.

* cited by examiner

SYSTEMS AND METHODS OF CAPTURING EYE-GAZE DATA

BACKGROUND

Traditional eye-gaze tracking systems collect eye-gaze data to calibrate accuracy of eye tracking. For example, some systems prompt an operator of a computing device to use a calibration application, which causes the computing device to display a gaze target (e.g., a red dot) at coordinates across the screen of the computing device. The operator is prompted to look at and follow the gaze target as the computing device moves the gaze target at different locations on the screen, one at a time, in an evenly distributed manner.

The traditional systems face issues of degrading accuracy with evenly distributed eye-gaze data. The degradation occurs particularly when the eyes look at locations that are at the edges the screen. Furthermore, a less number of neighboring eye-gaze target points in the training data near the screen boundaries cause the deep learning algorithm to predict an eye-gaze location less accurately. In practice, the less accurate prediction of eye-gaze points at edges and corners of the screen become significant when users use the edges and corners in common operations. For example, some of interactive system icons and buttons (e.g., a start button or a close button) appear at a corner of the screen (e.g., at lower left corner of the screen for start, upper right for close).

Increased accuracy in predicting eye-gaze locations would need more training data at select regions of the screen than other regions. Furthermore, capturing eye-gaze data as training data needs to complete at minimal time to prevent stress upon the operator doing the non-substantive operations (e.g., calibration of eye-gazing and not using applications for performing a desired task) on the computing device. Thus, developing a technology that better meets these requirements of capturing necessary eye-gaze training data and providing an ease of use would be desirable.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

According to the present disclosure, the above and other issues are resolved by generating a grid on a screen of a computing device with a series of regions with predetermined aspects in the grid and selecting a scan path that passes through one or more randomly generated gaze point within respective regions without crossing own path. Centers of the respective regions represent the overall average location or expected value over sample gaze points. The computing device displays an eye-gaze target that traverses along the path while guiding attention of the operator. The computing device captures a series of images or video image data as the operator follows the moving eye-gaze target, and determines eye-gaze locations as training data to train a gaze prediction model.

The gaze-point data indicate a uniform distribution over the series of regions in the grid on the screen. Areas of the respective regions toward the center of the screen are larger than areas of the regions adjacent to the corners and the edges of the screen to capture more eye-gaze data toward the corners and the edges of the screen while maintaining the uniform distribution over the series of regions in the grid. This way, the training data includes eye-gaze data with enhanced density near screen boundaries. The non-overlapping scan path prevents clustering of the training data. The non-overlapping scan path further minimizes the amount of time needed to capture the gaze-point data. Each gaze-point is captured once where the path covers the whole screen.

The scan path traverses across multiple screens as a combined screen when the computing device includes multiple displays. When the computing device includes multiple cameras, the present disclosure uses facial images from the multiple cameras and determines eye-gaze locations based on the multiple facial images for higher accuracy.

The methods further integrate an interactive mode in collecting eye-gaze data by interactively providing instructions to the user to perform specific actions (e.g., holding the face still, moving, and rotating the face, and the like).

This Summary is provided to introduce a selection of concepts in a simplified form, which is further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the following description and, in part, will be apparent from the description, or may be learned by practice of the disclosure.

BRIEF DESCRIPTIONS OF THE DRAWINGS

Non-limiting and non-exhaustive examples are described with reference to the following figures.

FIG. 1 illustrates an overview of an example system for capturing eye-gaze data as training data in accordance with aspects of the present disclosure.

FIGS. 2A-D illustrate examples of a series of regions in a grid on the screen in accordance with aspects of the present disclosure.

FIGS. 3A-B illustrate examples of a series of regions in a grid on the screen in accordance with aspects of the present disclosure.

FIG. 4 illustrates an example of a series of regions in a grid across multiple screens in accordance with aspects of the present disclosure.

FIGS. 5A-B illustrate examples of interactively capturing eye-gaze data in accordance with aspects of the present disclosure.

DETAILED DESCRIPTION

Figure 1:
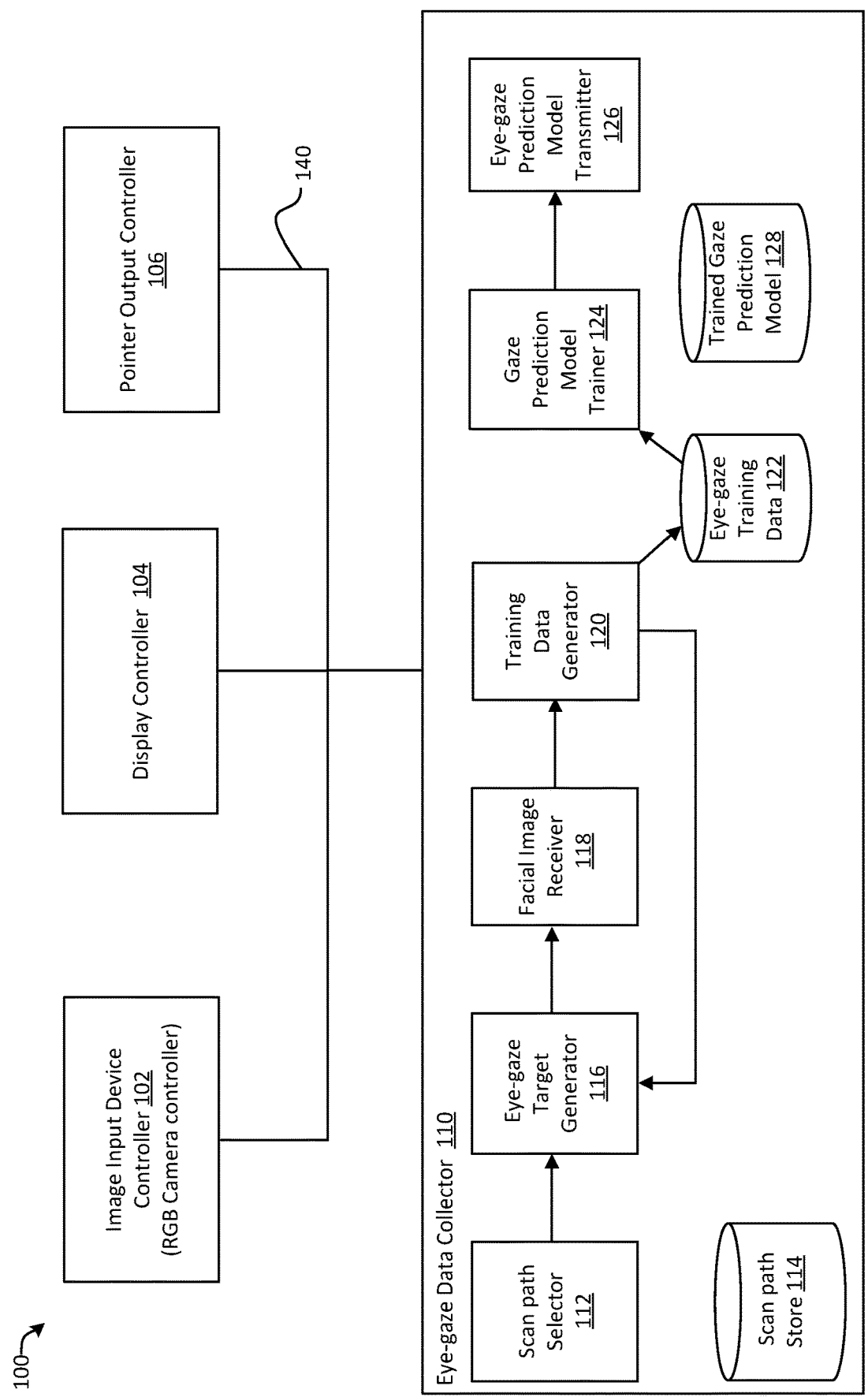

Various aspects of the disclosure are described more fully below with reference to the accompanying drawings, which from a part hereof, and which show specific example aspects. However, different aspects of the disclosure may be implemented in many different ways and should not be construed as limited to the aspects set forth herein; rather, these aspects are provided so that this disclosure will be thorough and complete and will fully convey the scope of the aspects to those skilled in the art. Aspects may be practiced as methods, systems, or devices. Accordingly, aspects may take the form of a hardware implementation, an entirely software implementation or an implementation combining software and hardware aspects. The following detailed description is, therefore, not to be taken in a limiting sense.

Predicting eye-gaze locations using an eye-gaze prediction model with accuracy depends on training data that include quality of camera(s) (e.g., both eyes, face, head-pose in space relative to the camera), illumination, background noise, and richness of training dataset (e.g., size and diversity).

As discussed in more detail below, the present disclosure relates to capturing eye-gaze data as training data for training an eye-gaze prediction model. In particular, the present technology includes selecting a scan path along which an eye-gaze target moves while capturing a video of an operator's facial image for determining an eye gaze location.

The present disclosure addresses the problem of capturing training data that improves accuracy in predicting eye-gaze locations. The disclosed technology enables capturing data for training the machine learning models, particularly based on a difference in terms. In aspects, generating training data may include data augmentation, which generates training data based on a small set of captured data. The disclosed technology captures eye-gaze data using an eye-gaze target that moves along a scan path. The scan path passes through a series of regions in a grid for capturing facial images at eye-gaze points. The eye-gaze points are uniformly and randomly distributed in respective regions. Dimensions of the regions may be adjusted to raise density of the eye-gaze points. In aspects, areas of the regions along edges and corners of the screen may be smaller than the edges and corners toward center of the screen to capture more eye-gaze data in toward the edges and corners. The screen may be an aggregate screen that includes multiple screens. Facial images from multiple cameras with different wavelength sensitivity (e.g., visible spectrum or infrared) may be captured for generating training data. The disclosed technology may enhance variations of facial images by interactively instructing the operator to make specific actions associated with the face and receives additional facial images based on the actions by the operator. The disclosed technology may also track the quality and diversity of the acquired data against the desired benchmarks and present the operator with the appropriate capture modes accordingly.

FIG. 1 illustrates an overview of an example system 100 for capturing eye-gaze data for training an eye-gaze prediction model in accordance with aspects of the present disclosure. System 100 represents a system using a grid with a series of regions and a scan path that passes through centers of respective regions of the series of regions for displaying an eye-gaze target. System 100 includes an image input device controller 102, a display controller 104, a pointer output controller 106, an eye-gaze data collector 110, and a data bus 140 that connects the eye-gaze data collector 110 with respective controllers.

The image input device controller 102 controls one or more image input devices (e.g., an RGB/visible light camera, IR camera, etc.). In aspects, the RGB camera captures image frames for facial images and/or video stream of a face of an operator operating the computing device. In some aspects, the image input device controller 102 controls and concurrently captures image frames from multiple image input devices. In aspects, the disclosed technology may include existing and or future camera technology including pulsed emitters (e.g., light emitting diodes) which may be used to enhance accuracy and precision of results and mitigate for low environment lighting or high light interference (e.g., sunlight) and/or dynamic shutters or filters.

The display controller 104 controls a screen of the computing device. The display controller 104 may display an eye-gaze indicator (e.g., a pointer output) that indicates where the operator is looking at. The display controller 104 may also display an eye-gaze target (e.g., a red dot icon) to prompt and guide the operator to look at a specific location of the screen.

The pointer output controller 106 controls a location and a shape of the pointer output on the screen of the computing device. In aspects, the pointer output may represent where the operator is looking at on the screen of the computing device. In some other aspects, the pointer output may represent a cursor of a mouse and other pointing devices.

The eye-gaze data collector 110 includes a scan path selector 112, a scan path store 114, an eye-gaze target generator 116, a facial image receiver 118, an eye-gaze training data generator 120, eye-gaze training data database 122. The eye-gaze data collector 110 further includes an eye-gaze prediction model trainer 124, a trained eye-gaze prediction model 128, and an eye-gaze prediction model transmitter 126.

The scan path selector 112 selects a scan path from the scan path store 114. The scan path store 114 stores a set of predefined scan paths. In aspects, a scan path represents a path that passes through uniformly and randomly generated gaze targets in the respective regions of the series of regions of the grid on the screen of the computing device. A center of a region represents an expected value of uniformly distributed random points in the region. By capturing eye-gaze data around the centers of the regions, the system 100 generates training data with a uniform distribution on the screen of the computing device. Some scan paths pass through corners and along edges of the screen in a longer duration than other scan paths. In aspects, the scan path selector 112 may select a particular scan path at random. Providing variations in moving the eye-gaze target at different times may keep the operator's attention. Additionally or alternatively, the scan paths have none or a minimal abrupt change in the directions of gaze target movement. The reduced or eliminated abrupt change makes it easier for the operator to follow and mimic a more real-world setting of user interface. The scan path selector 112 may select a scan path passes through near corners and along edges of the display when the distribution of the captured eye-gaze locations indicate a scarcity of the captured eye-gaze locations near the corners and along the edges.

In aspects, the disclosed technology generates a grid with a series of regions based on an aspect ratio of the screen of the computing device. A dimension of the grid may be, for example, four by three when an aspect ratio of the screen is 16:9, generating a total of twelve regions. The series of regions may be of equal size. Additionally, or alternatively, regions along the edges and the corners of the screen may be smaller in area than other regions in the grid.

The eye-gaze target generator 116 generates an eye-gaze target that moves along the selected scan path. In aspects, the eye-gaze target moves along the scan path at a constant velocity. In some other aspects, the eye-gaze target moves in varying speeds, slower as the eye-gaze target is in proximity of corners of the screen and making sharp turns. In aspects, the eye-gaze target may be a symbol (e.g., an icon) that keeps attention by the operator. The eye-gaze target generator 116 further indicates the eye-gaze target on a screen of the computing device. In aspects, the eye-gaze target generator 116 transmits instructions the display controller 104 to display the eye-gaze target on the screen of the computing device. In some aspects, the system 100 displays the eye-gaze target without displaying the scan path. By not displaying the eye-gaze target without the scan path, the system 100 enables the operator to focus on following the eye-gaze target as the eye-gaze target moves across the screen.

The facial image receiver 118 receives a facial image from the image input device controller 102. The facial image includes a face of the operator following the eye-gaze target on the screen of the computing device. In aspects, a camera associated with the computing device captures the facial image. In aspects, the facial image receiver 118 continuously receives the facial image as frames in a video data stream while the eye-gaze target moves along the scan path. In contract, the traditional system may capture facial images when the system displays the eye-gaze target at randomly generated coordinates. The continuous receiving of the facial images as a video stream enables capturing variations and additional data points for in training data.

The eye-gaze training data generator 120 generates eye-gaze training data based on a location information of the eye-gaze target and the received facial image data in which the operator is looking at the symbol. The eye-gaze training data generator 120 stores the training data in the eye-gaze training data database 122.

The eye-gaze prediction model trainer 124 trains a gaze prediction model using the eye-gaze training data database 122. In aspects, the eye-gaze prediction model trainer 124 updates parameters of a convolutional neural network and a series of fully connected neural networks based on the eye-gaze training data database 122. The eye-gaze prediction model trainer 124 stores the parameters for the neural networks in the trained eye-gaze prediction model 128. In aspects, the eye-gaze training data database 122 may depend on the operator.

The eye-gaze prediction model transmitter 126 transmits the trained eye-gaze prediction model 128 to an eye-gaze tracker (not shown) for deployment.

As will be appreciated, the various methods, devices, applications, features, etc., described with respect to FIG. 1 are not intended to limit the system 100 to being performed by the particular applications and features described. Accordingly, additional controller configurations may be used to practice the methods and systems herein and/or features and applications described may be excluded without departing from the methods and systems disclosed herein.

Figures 2A, 2B:
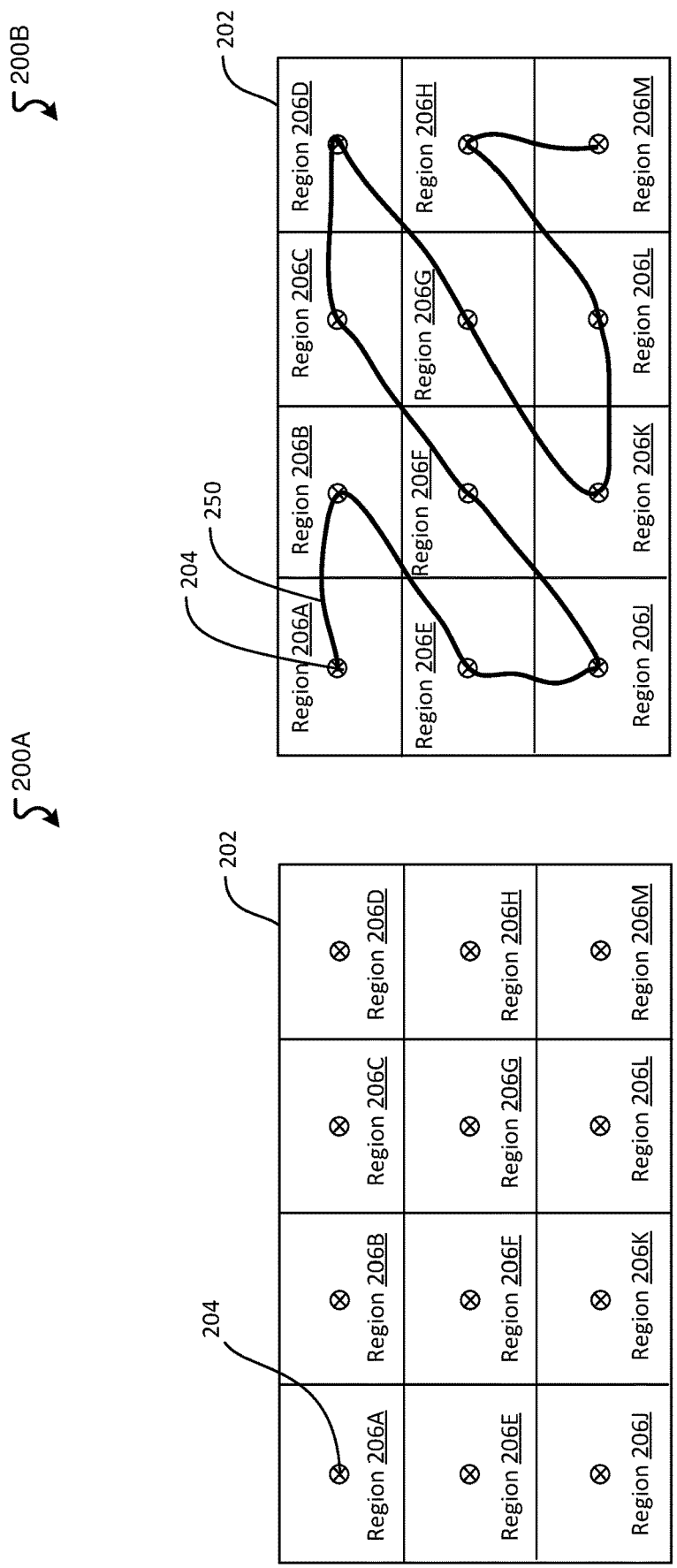

FIGS. 2A-B illustrate examples of a series of regions of a grid in accordance with aspects with aspects of the present disclosure. FIG. 2A illustrates an example of a grid 202 with a series of regions (regions 206A-M) on a screen of a computing device. In aspects, the regions in the grid may be equal in areas with the same aspect ratio as the screen. For example, the screen may be 16:9 in the aspect ratio, and the grid may be 4 by 3. Accordingly, each of the regions in the grid may have the same aspect ratio of 4:3. A center 204 (or a primary target point) of the region 206A is a location that represent an expected value of uniformly distributed points in the region 206A.

FIG. 2B illustrates an example of a grid 202 with a scan path 250 where the eye-gaze target moves along the scan path while capturing eye-gaze data for training the eye-gaze prediction model. The scan path 250 starts at the center of the region 206A and passes through centers of a series of regions: starting at region 206A, followed by region 206B, region 206E, region 206J, region 206F, region 206C, region 206D, region 206G, region 206K, region 206L, region 206H, and region 206M. The scan path 250 ends at the center of the region 206M. In some aspects, the scan path 250 passes through the uniformly and randomly generated gaze target in the particular the regions only once. In aspects, the center of each region shows the average location of gaze point within that region. In practice, the gaze points are generated randomly within each region for training to achieve greater diversity in the dataset. During calibration these centers could be directly used as is The traditional system displays a symbol at the target coordinates on the screen and captures a facial image as the operator looks at the symbol. In contrast, the disclosed technology here moves the symbol along the path, and captures images while the operator follows the moving symbol. The captured eye-gaze data in the disclosed technology still maintain randomness of data points because the scan path passes through uniformly and randomly generated gaze targets of all the regions across the screen. The disclosed technology captures variations of eye-gaze data and additional data points in training data.

In aspects, the scan path 250 is generally without crossing (e.g., intersecting) its own path. Capturing eye-gaze data along the non-overlapping path prevents the eye-gaze data from forming clusters. The clusters may form when the training data includes multiple facial images from the same eye-gaze location. Each point on the non-overlapping path is unique to all other points on the path.

Figures 2C, 2D:
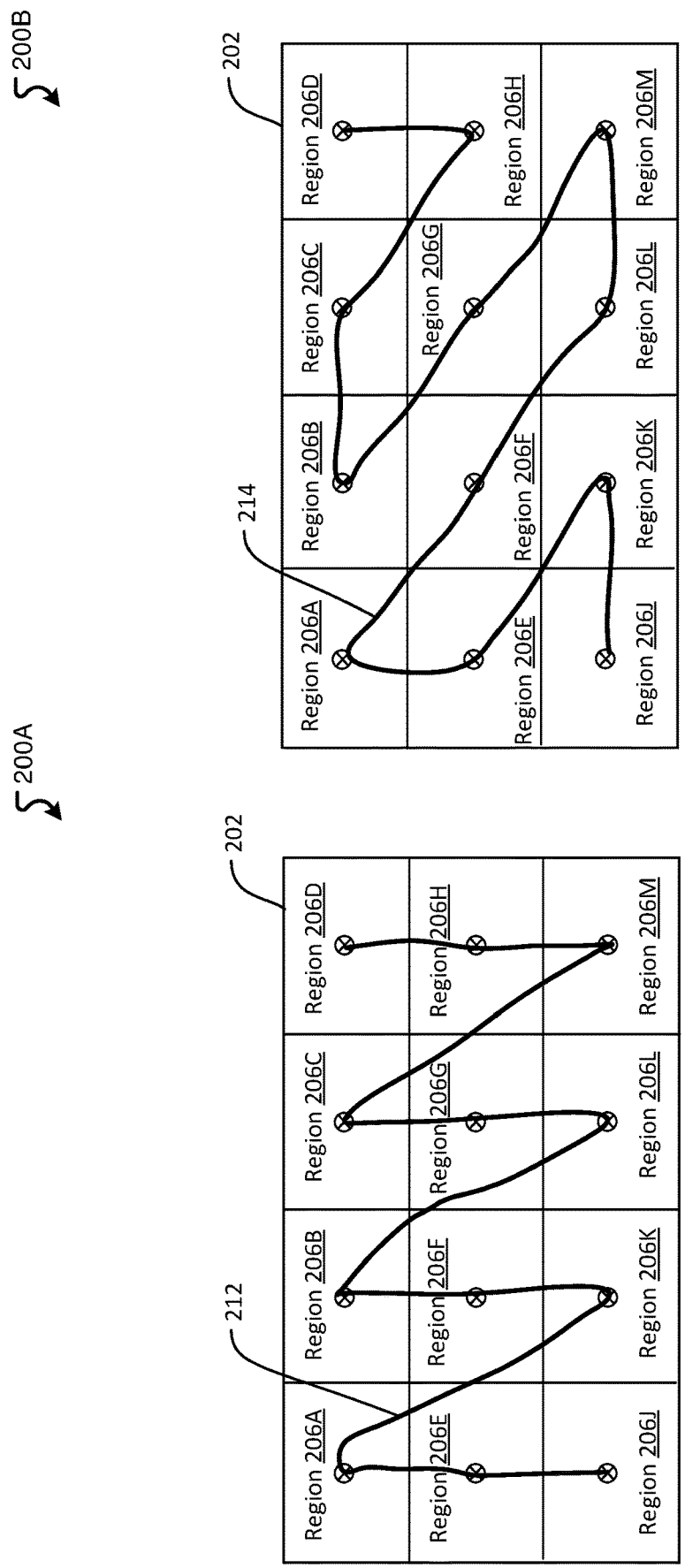

FIG. 2C illustrates another example of a scan path in the grid on the screen in accordance with aspects of the present disclosure. The grid 202 includes twelve regions (e.g., regions 206A-M). In aspects, a scan path 212 starts at the center of region 206J, followed by region 206E, region 206A, region 206K, region 206F, region 206B, region 206L, region 206G, region 206C, region 206M, region 206H, and region 206D. Alternative scan paths reduces likelihood of the data collection becoming mundane tasks for the operators to follow the eye-gaze target moving in a same pattern. Furthermore, it brings enhanced spatial coverage in the acquired training data set.

FIG. 2D illustrates yet another example of a scan path in the grid on the screen in accordance with aspects of the present disclosure. The grid 202 includes twelve regions (e.g., regions 206A-M). In aspects, a scan path 214 starts at the center of region 206J, followed by region 206K, region 206E, region 206A, region 206F, region 206L, region 206M, region 206G, region 206B, region 206C, region 206H, and region 206D. In aspects, the present disclosure maintains multiple scan paths in a database (e.g., the scan path store 114 in FIG. 1).

Figure 3A:
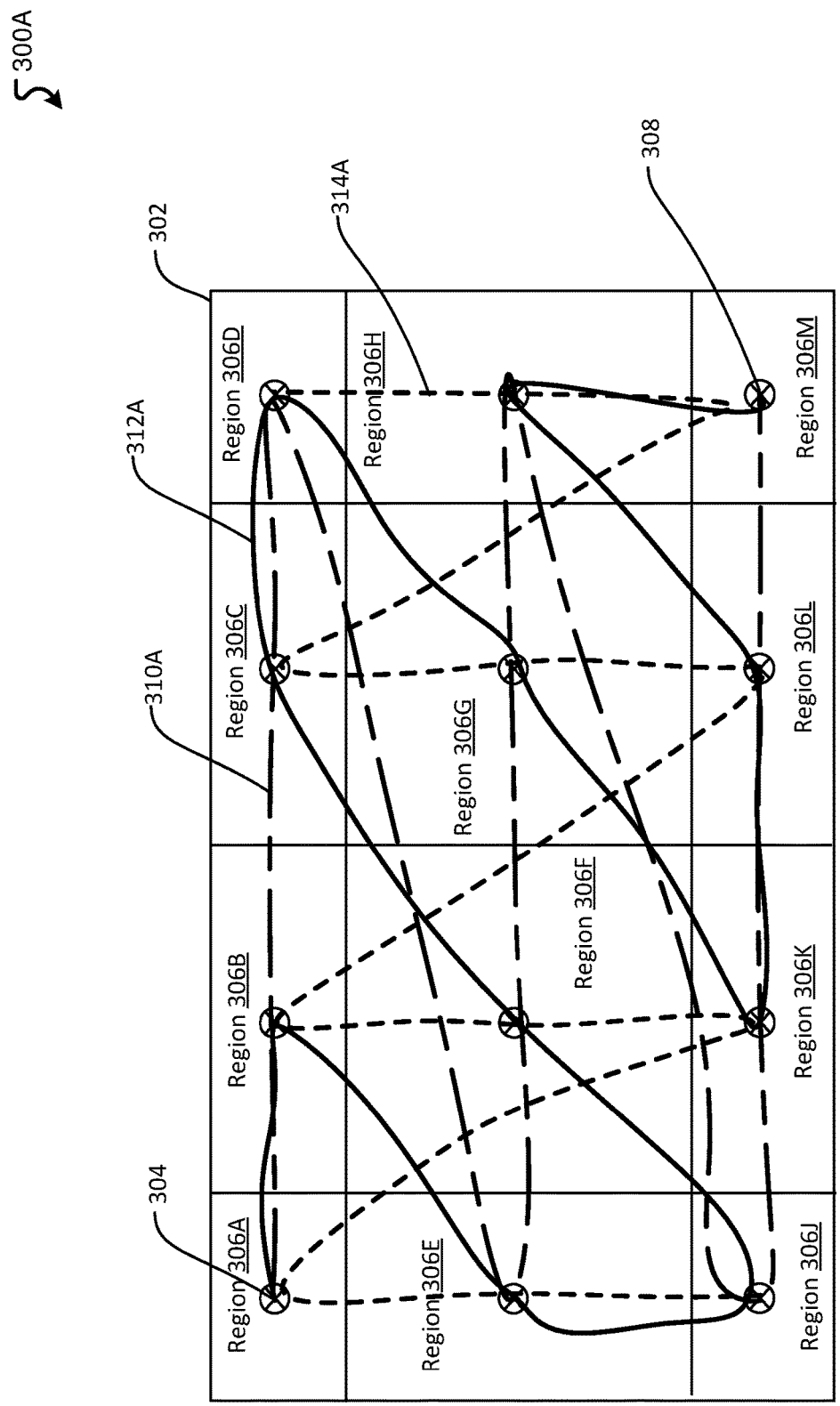

FIG. 3A illustrates an example of a set of scan paths in a grid on the screen in accordance with aspects of the present disclosure. Some traditional systems often suffer from having low-density data at boundaries of the screen when collecting training data. In practice, as the operator's visual focus moves away from the camera on the screen, in some systems there may be an intrinsic decay in resolution, which negatively influences accuracy of determining an eye-gaze location. Having low-density data at boundaries of the screen worsens the problem because of a lack of data points in areas where the intrinsic resolution decay occurs. The present disclosure forces more data acquisition toward device boundaries (e.g., edges and corners) by reducing areas of some regions than others and repositioning centers of respective regions on the screen. In particular, the disclosed technology generates a grid such that those regions that are adjacent to edges and corners of the screen are smaller in areas than the regions that are not adjacent to the edges and the corners.

In aspects, the screen has an aspect ratio of 16:9. A grid may include twelve regions with respective horizontal edges with lengths 3:5:5:3 and respective vertical edges with lengths 2:5:2. In FIG. 3A, a grid 302 includes twelve regions. Region 306A and region 306D have an aspect ratio of 2:3, region 306B and region 306C having the aspect ratio of 2:5, region 306E and region 306H having the aspect ratio of 5:3, region 306F and region 306G having the aspect ratio of 5:5, region 306J and region 306M having the aspect ratio of 2:3, and region 306K and 306L having the aspect ratio of 2:5.

A scan path 310A (as shown in a partially dotted path) connects a center 304 of the region 306A and a center 308 of the region 306M, passing through other centers of regions in the grid 302. A scan path 312A (as shown in a solid path) also connects the same points as the scan path 310A but in a diagonal manner. A scan path 314A (as shown in a dotted path) passes through the same set of the centers but starts from region 306J and ends in the region 306M, traversing vertically.

Figure 3B:
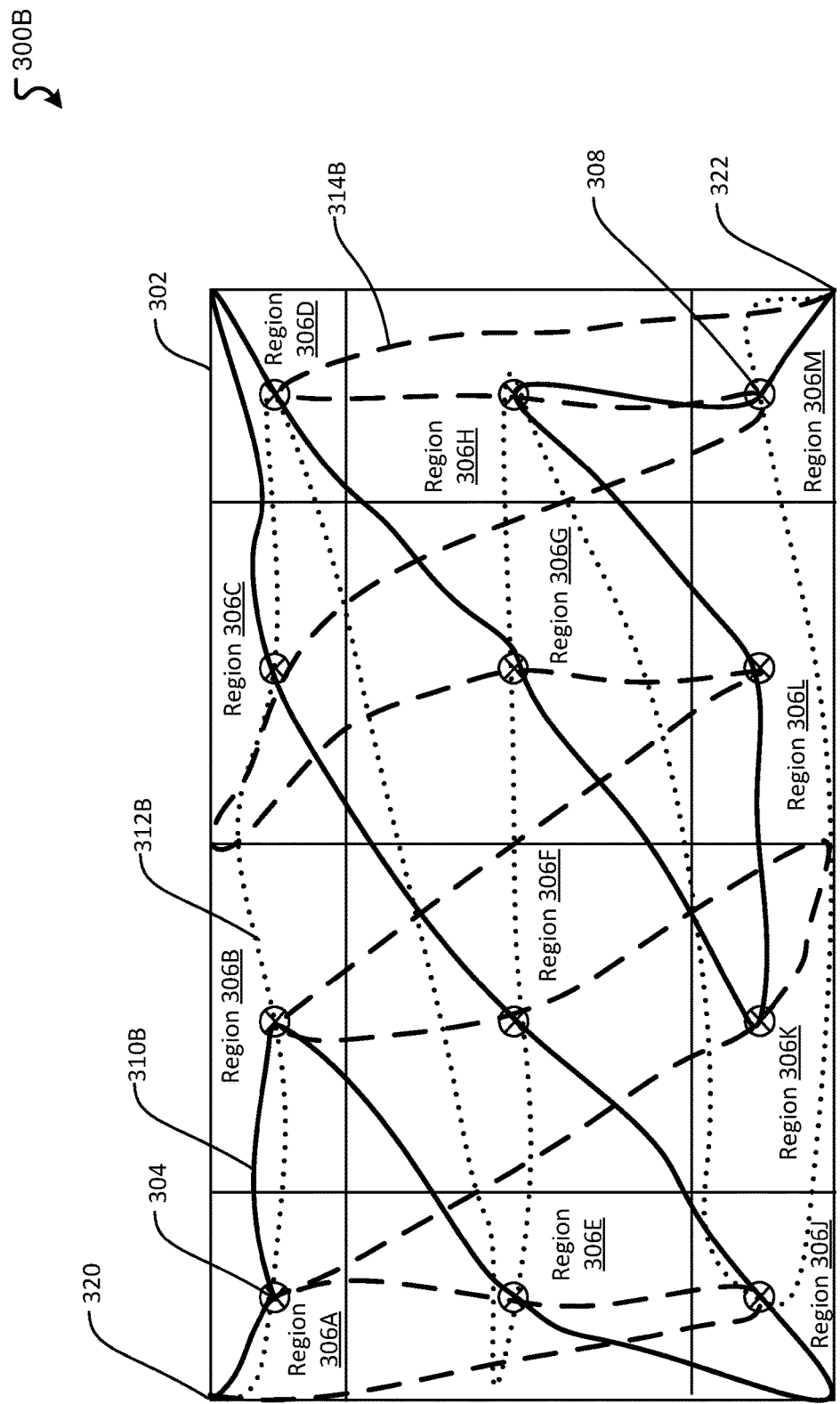

FIG. 3B illustrates an example of a set of scan paths in a grid passing the corners and the edges of the screen for capturing eye-gaze data points in locations near the corners and the edges. In aspects, the disclosed technology further enhances capturing eye-gaze data in proximities of edges and corners of the screen by designing the scan paths pass through corners and edges while also passing through centers of respective regions in the grid. In the grid 302, there are twelve regions, where the regions that are adjacent to the edges and the corners of the grid 302 have smaller areas than the regions toward the center of the grid 302. FIG. 3B includes an example of three scan paths: scan path 310B (shown in a solid path), scan path 312B (shown in a fine dotted path), and scan path 314B (shown in a medium dotted path).

In aspects, the three scan paths respectively start at the upper left corner 320 of the region 306A and ends at the lower right corner 322 of the region 306M. Each scan path passes through centers of the twelve regions in a sequence that is distinct from other scan paths. Additionally or alternatively, respective scan paths pass in proximity of edges and corners of the screen.

Figure 4:
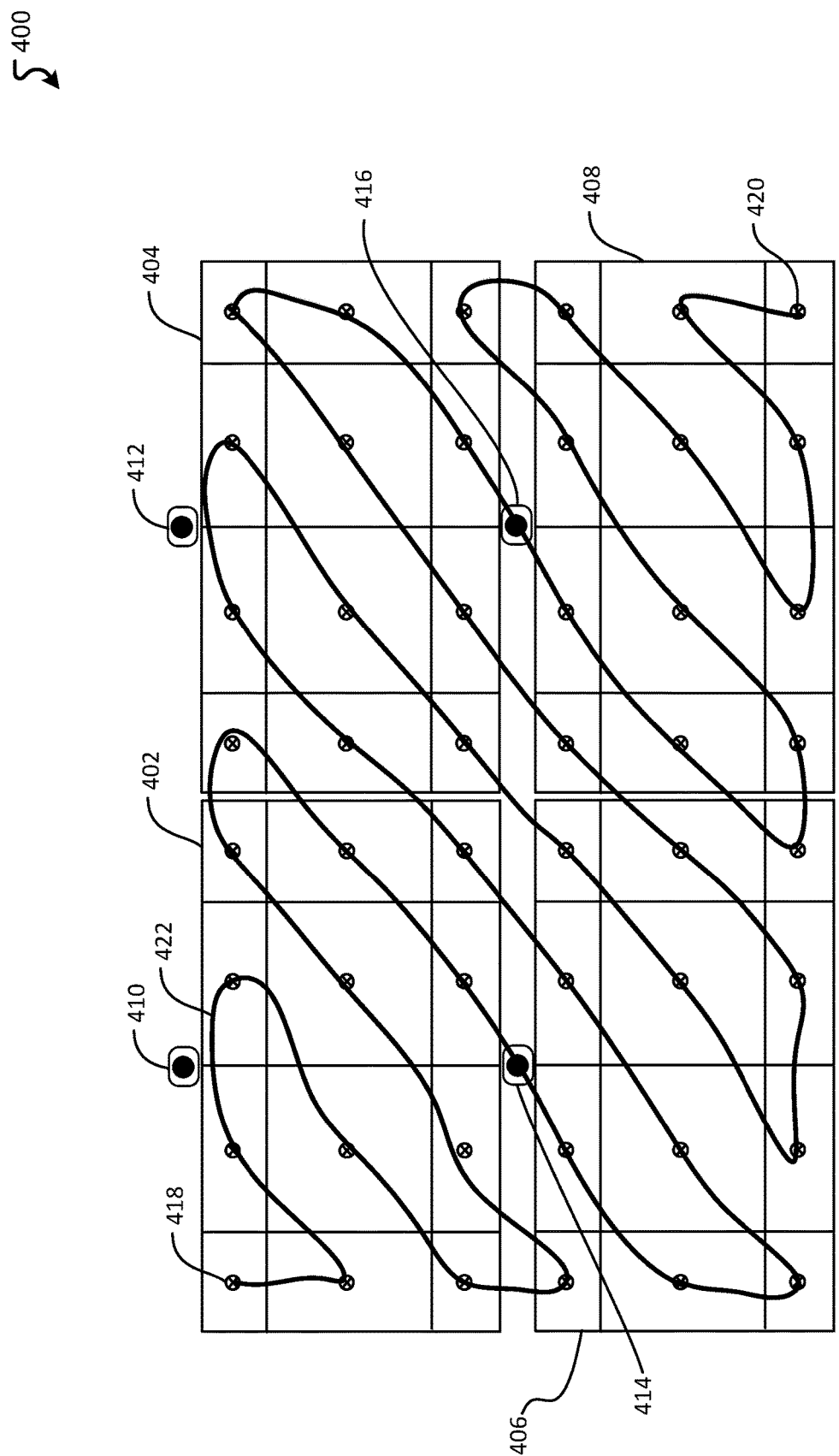

FIG. 4 illustrates an example of a scan path across multiple displays according to aspects of the present disclosure. The example 400 illustrates a screen based on a combination of four displays in a two-by-two matrix form: an upper left display 402, an upper right display 404, a lower left display 406, and a lower right display 408. The four displays form as one screen for the operator of the computing device (and/or computing devices) to interact using eye-gaze.

A scan path 422 connects a center 418 of an upper left region of the upper left display 402 and a center 420 of a lower right region of the lower right display 408. The scan path 422 passes through regions in across respective displays in a diagonal manner, without crossing own scan path, passing centers of respective regions once. Traditional systems typically calibrate eye-gaze tracking among displays independently. The disclosed technology generates a scan path that passes across the multiple displays as one screen for capturing eye-gaze data for training and calibration.

In aspects, the multiple displays may include multiple cameras for capturing facial images. The disclosed technology captures the facial images using the multiple cameras. Training an eye-gaze prediction model using facial images from multiple cameras as training data enhances accuracy in predicting eye-gaze locations because of more feature data for eye-gazing based on the multiple facial images than one facial image. In aspects, four facial images from a camera 410 that is attached to the upper left display 402, a camera 412 attached to the upper right display 404, a camera 414 attached to the lower left display 406, and a camera 416 attached to the lower right display 408. In aspects, a display may include none, one, or multiple cameras. Locations of the cameras are not limited to the top-center of the display. For example, a camera may be placed behind the screen, pointed through the screen.

In some aspects, the disclosed technology simultaneously captures all four video streams of facial images from the four cameras throughout a period when the symbol moves across the four displays along the scan path. In some other aspects, the system may weigh more on a facial image captured by a camera of a display in which the system displays the symbol than facial images captures by other cameras. Traditional system may process eye-gaze data captured by a camera as out-of-screen when the symbol is off-screen from the display. The disclosed technology using facial images from multiple cameras is particularly effective when the computing device places multiple displays in adjacent to each other in angles, collectively forming a "curved" screen. In use of the "curved" screen, use of video streams from the four cameras from different directions improves accuracy even when angular movement of gaze makes a long stride across the displays. Features of some of facial images from the multiple facial images may compensate for errors in other facial images.

Figure 5:
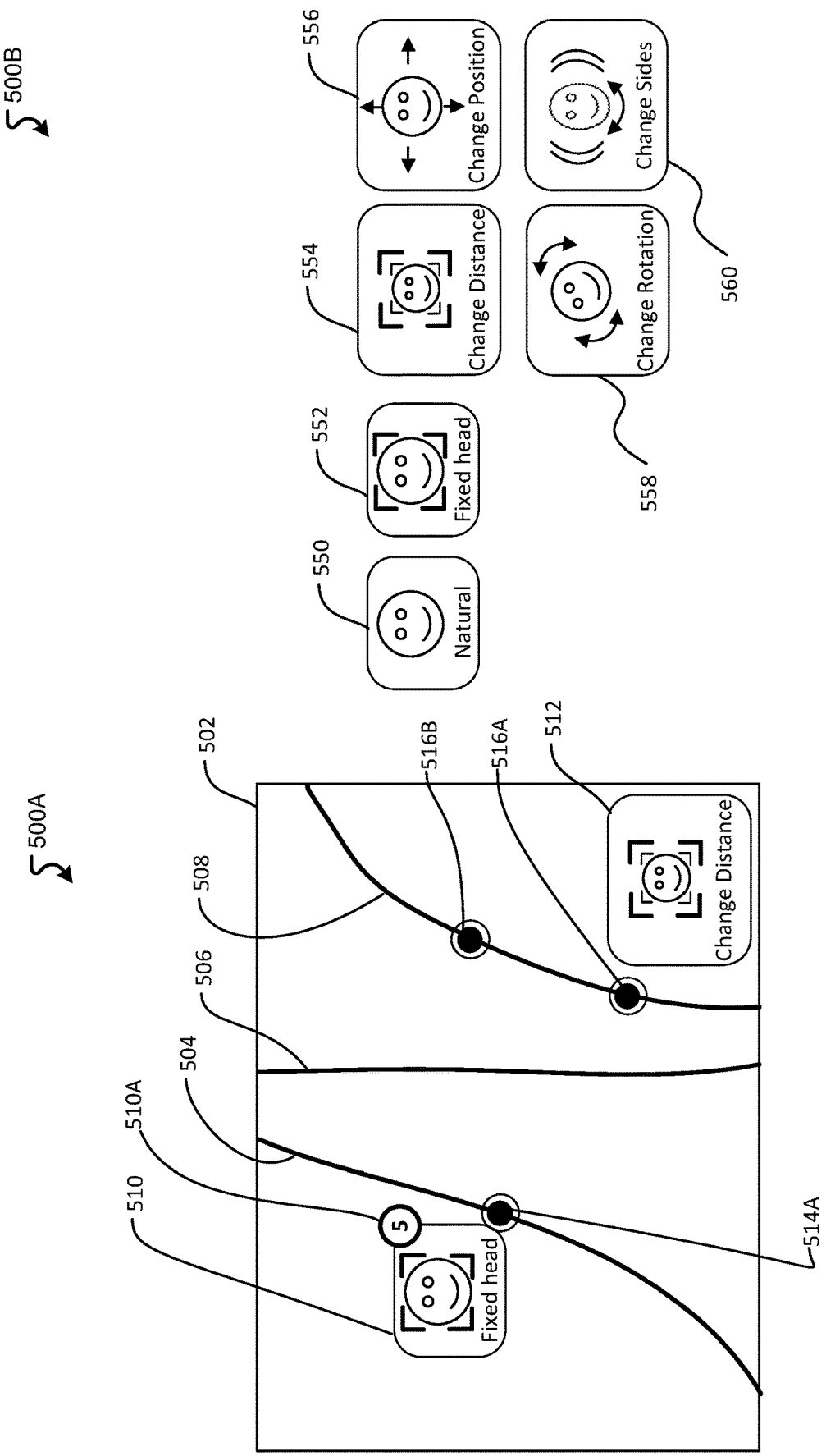

FIGS. 5A and 5B illustrate examples of interactive eye-gaze capturing system. Enhancing training data for deep learning of eye-gaze tracking includes improving a quality, a diversity, and variations of eye-gaze data. Variations of training data may include illuminations, distance from camera, head rotation, head pose, and the like. The variation may depend on operators of the computing devices. The disclosed technology may include an icon-based interactive process that prompts the operator to perform specific action as the system captures a video steam of facial images. In aspects, the actions include holding the head still, changing a distance of the face from the camera, changing a position of the face in the facial image being captured by the camera, rotating the face, changing sides of the face, and the like.

FIG. 5A illustrates an example of a part of a screen according to the aspects of the present disclosure. An example 500A includes a partial screen 502 showing scan path 504, scan path 506, and scan path 508, in a time lapse for illustrating movement of the eye-gaze target at various times. An eye-gaze target 514A stops after moving along the scan path 504.

The exemplar icon 510 instructs the operator to hold the head still for the upcoming phase of data acquisition. The number 510A indicates a remaining time after which the next phase begins. No facial imagery is captured during this time (or if captured marked to be discarded) as the user spends this time to read the icon instructions and has attention away from the eye-gaze target (stimulus). The color of the eye-gaze target may change (e.g. grey, dull red etc.) to indicate that no data is being captured. After the five seconds lapse, the exemplar icon 510 may disappear from the partial screen 502 and the eye-gaze target 514A resume moving along the scan path 504, capturing images in this new mode. In aspects, the scan path 504 does not appear on the partial screen 502; the operator may just see the eye-gaze target 514A moving at a constant speed as the operator follows. In aspects, there may be one eye-gaze target being displayed on the partial screen at a time for guiding the operator's focus on the eye-gaze target.

Similarly, an eye-gaze target 516A stops on the scan path 508. An exemplar icon 512 appears. The exemplar icon 512 instructs the operator to change distance (e.g., closer to and further from the screen (and/or the camera). The eye-gaze target 516A then resumes its movement along the scan path (e.g., an eye-gaze target 516B). The system captures a video stream of the facial image throughout the operator interactively follows the eye-gaze target and performs actions as directed at times. In aspects, the disclosed technology integrates sampling of facial images of the operators at different angles and distance into the eye-gaze sampling. The integration may reduce time needed to collect information about the operator while keeping the operator's attention on the screen.

FIG. 5B illustrates an example of icons that interactively instruct the operator to perform specific actions while capturing eye-gaze data according to the aspects of the present disclosure. An icon 550 instructs the operator to hold a natural expression to the camera. An icon 552 instructs the operator to hold the head still. An icon 554 instructs the operator to change distance to the screen and/or the camera by moving closer or further from the screen and/or the camera. An icon 556 instructs the operator to change a position of the face (e.g., moving to the left, to the right, to above and to below). An icon 558 instructs the operator to rotate the face (e.g., tilting the face). An icon 560 instructs the operator to change sides (e.g., looking to the right, and looking to the left).

Figure 6:
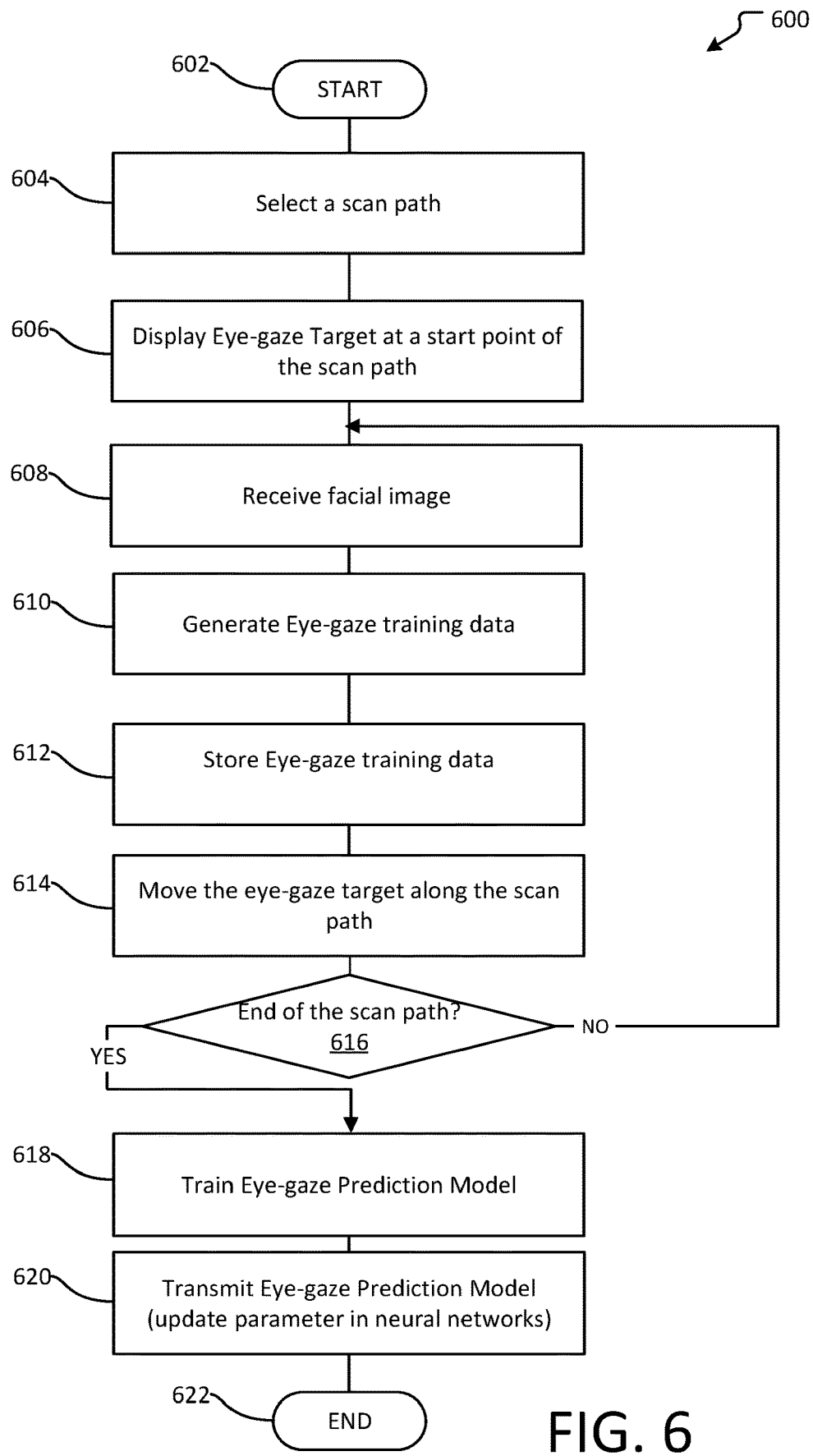
FIG. 6 illustrates an example of a method for capturing eye-gaze data for training an eye-gaze prediction model in accordance with aspects of the present disclosure.

FIG. 6 is an example of a method for capturing eye-gaze data for generating training data for training an eye-gaze prediction model in accordance with aspects of the present disclosure. A general order of the operations for the method 600 is shown in FIG. 6. Generally, the method 600 begins with start operation 602 and ends with end operation 622. The method 600 may include more or fewer steps or may arrange the order of the steps differently than those shown in FIG. 6. The method 600 can be executed as a set of computer-executable instructions executed by a computer system and encoded or stored on a computer readable medium. Further, the method 600 can be performed by gates or circuits associated with a processor, an ASIC, an FPGA, a SOC or other hardware device. Hereinafter, the method 600 shall be explained with reference to the systems, components, devices, modules, software, data structures, data characteristic representations, signaling diagrams, methods, etc., described in conjunction with FIGS. 1, 2, 3, 4, 5, 7, and 8A-B.

Following start operation 602, the method 600 begins with select operation 604, which selects a scan path. In aspects, the select operation 604 may select the scan path from a set of scan paths stored in a scan path store. In aspects, the select operation 604 may select different scan path at different times for the operator to increase variations of eye-gazing data for training.

Display operation 606 displays a symbol at a start point of the scan path on the screen. In aspects, the symbol may indicate a red dot or some other shape stand out on the screen for the operator to maintain a focus. In some aspects, the display operation 606 displays the symbol without display-ing the scan path. This way, the operator has less distraction while following the symbol on the screen.

Receive operation 608 receives a facial image of the operator. In aspects, the receive operation 608 receives a video stream of the facial image of the operator as the symbol moves on the screen. Respective frames of the facial image correspond to respective locations of the symbol.

Generate operation 610 generates eye-gaze training data. In aspects, the eye-gaze training data include a facial image and a location information of the symbol. The location information is true data. The training data is for training an eye-gaze prediction model to predict an eye-gaze location to be the location based on the facial image.

Store operation 612 stores the eye-gaze training data in the eye-gaze training data database (e.g., the eye-gaze training data database 122 in FIG. 1). In aspects, the eye-gaze training data includes one or more facial images associated with a correct eye-gaze location. The eye-gaze training data include diversity of situations and variations of facial images of the operator to train the eye-gaze prediction model for a variety of usage situations. For example, use of a smart phone and a tablet as a computing device involves a variety of usage scenes (e.g., positions and angles of holding the smart phone, variance in lighting at different times and locations, and facial angles and expressions at time of use).

Move operation 614 moves the symbol along the scan path. In aspects, the move operation 614 moves the symbol at a constant velocity across the screen. The velocity may be slow enough for the operator following the moving symbol easily. Furthermore, the velocity may be fast enough to minimize the time to maintain the operator's attention to the moving symbol.

The decision operation 616 decides whether the symbol is at the end of the scan path. When the symbol is not at the end of the scan path, the method 600 proceeds to the receive operation 608 and repeats the steps of capturing new eye-gaze data and storing a new training data based on the new eye-gaze data. When the symbol is at the end of the scan path, the method 500 may proceed to a train operation 618. Additionally or alternatively, the method 600 may receive a facial image that corresponds to the symbol at the end of the scan path, generate, and store new training data.

The train operation 618 trains an eye-gaze prediction model based on the training data through deep learning. In aspects, the train operation 618 generates parameters for a set of a convolutional neural network and fully connected neural networks. In some aspects, the train operation 618 trains the model for optimizing the model for a particular operator as a target user of a computing device. For example, smart phones are typically used by an operator and rarely shared with other users.

Transmit operation 620 transmit the trained eye-gaze prediction model for deployment. In aspects, the transmit operation 620 includes updating the set of a convolutional neural network and fully connected neural networks with parameters in the trained eye-gaze prediction model. In aspects, method 600 may end with end operation 622.

As should be appreciated, operations 602-622 are described for purposes of illustrating the present methods and systems and are not intended to limit the disclosure to a particular sequence of steps, e.g., steps may be performed in different order, additional steps may be performed, and disclosed steps may be excluded without departing from the present disclosure.

Figure 7:
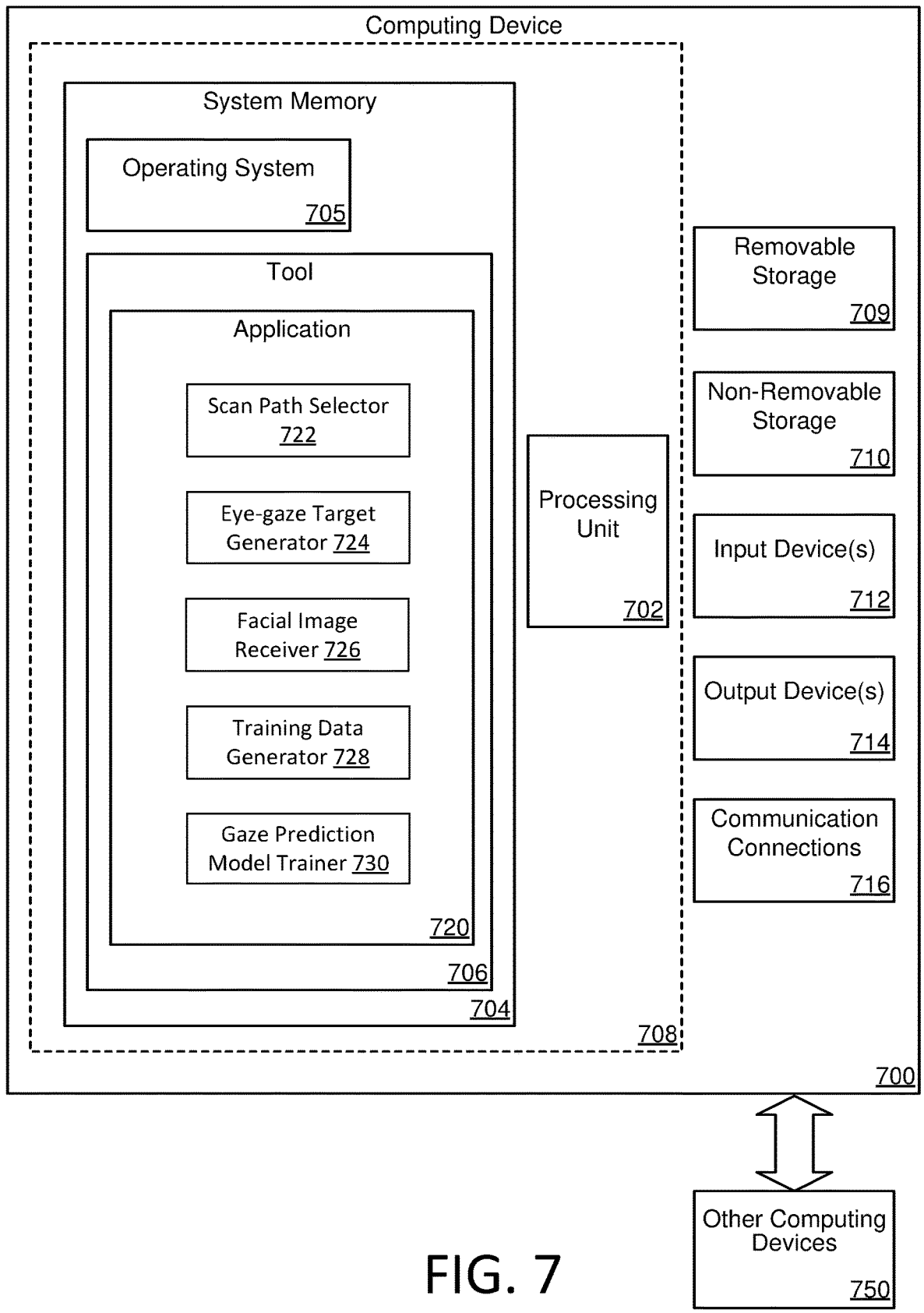
FIG. 7 is a block diagram illustrating example physical components of a computing device with which aspects of the disclosure may be practiced.

FIG. 7 is a block diagram illustrating physical components (e.g., hardware) of a computing device 700 with which aspects of the disclosure may be practiced. The computing device components described below may be suitable for the computing devices described above. In a basic configuration, the computing device 700 may include at least one processing unit 702 and a system memory 704. Depending on the configuration and type of computing device, the system memory 704 may comprise, but is not limited to, volatile storage (e.g., random access memory), non-volatile storage (e.g., read-only memory), flash memory, or any combination of such memories. The system memory 704 may include an operating system 705 and one or more program tools 706 suitable for performing the various aspects disclosed herein such. The operating system 705, for example, may be suitable for controlling the operation of the computing device 700. Furthermore, aspects of the disclosure may be practiced in conjunction with a graphics library, other operating systems, or any other application program and is not limited to any particular application or system. This basic configuration is illustrated in FIG. 7 by those components within a dashed line 708. The computing device 700 may have additional features or functionality. For example, the computing device 700 may also include additional data storage devices (removable and/or non-removable) such as, for example, magnetic disks, optical disks, or tape. Such additional storage is illustrated in FIG. 7 by a removable storage device 709 and a non-removable storage device 710.

As stated above, a number of program tools and data files may be stored in the system memory 704. While executing on the at least one processing unit 702, the program tools 706 (e.g., an application 720) may perform processes including, but not limited to, the aspects, as described herein. The application 720 includes a scan path selector 722, an eye-gaze target generator 724, a facial image receiver 726, an eye-gaze training data generator 728, and an eye-gaze prediction model trainer 730, as described in more detail with regard to FIG. 1. Other program tools that may be used in accordance with aspects of the present disclosure may include electronic mail and contacts applications, word processing applications, spreadsheet applications, database applications, slide presentation applications, drawing or computer-aided application programs, etc.

Furthermore, aspects of the disclosure may be practiced in an electrical circuit comprising discrete electronic elements, packaged or integrated electronic chips containing logic gates, a circuit utilizing a microprocessor, or on a single chip containing electronic elements or microprocessors. For example, aspects of the disclosure may be practiced via a system-on-a-chip (SOC) where each or many of the components illustrated in FIG. 7 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 700 on the single integrated circuit (chip). Aspects of the disclosure may also be practiced using other technologies capable of performing logical operations such as, for example, AND, OR, and NOT, including but not limited to mechanical, optical, fluidic, and quantum technologies. In addition, aspects of the disclosure may be practiced within a general purpose computer or in any other circuits or systems.

The computing device 700 may also have one or more input device(s) 712, such as a keyboard, a mouse, a pen, a sound or voice input device, a touch or swipe input device, etc. The output device(s) 714 such as a display, speakers, a printer, etc. may also be included. The aforementioned devices are examples and others may be used. The computing device 700 may include one or more communication connections 716 allowing communications with other computing devices 750. Examples of suitable communication connections 716 include, but are not limited to, radio frequency (RF) transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program tools. The system memory 704, the removable storage device 709, and the non-removable storage device 710 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 700. Any such computer storage media may be part of the computing device 700. Computer storage media does not include a carrier wave or other propagated or modulated data signal.

Communication media may be embodied by computer readable instructions, data structures, program tools, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Figure 8A:
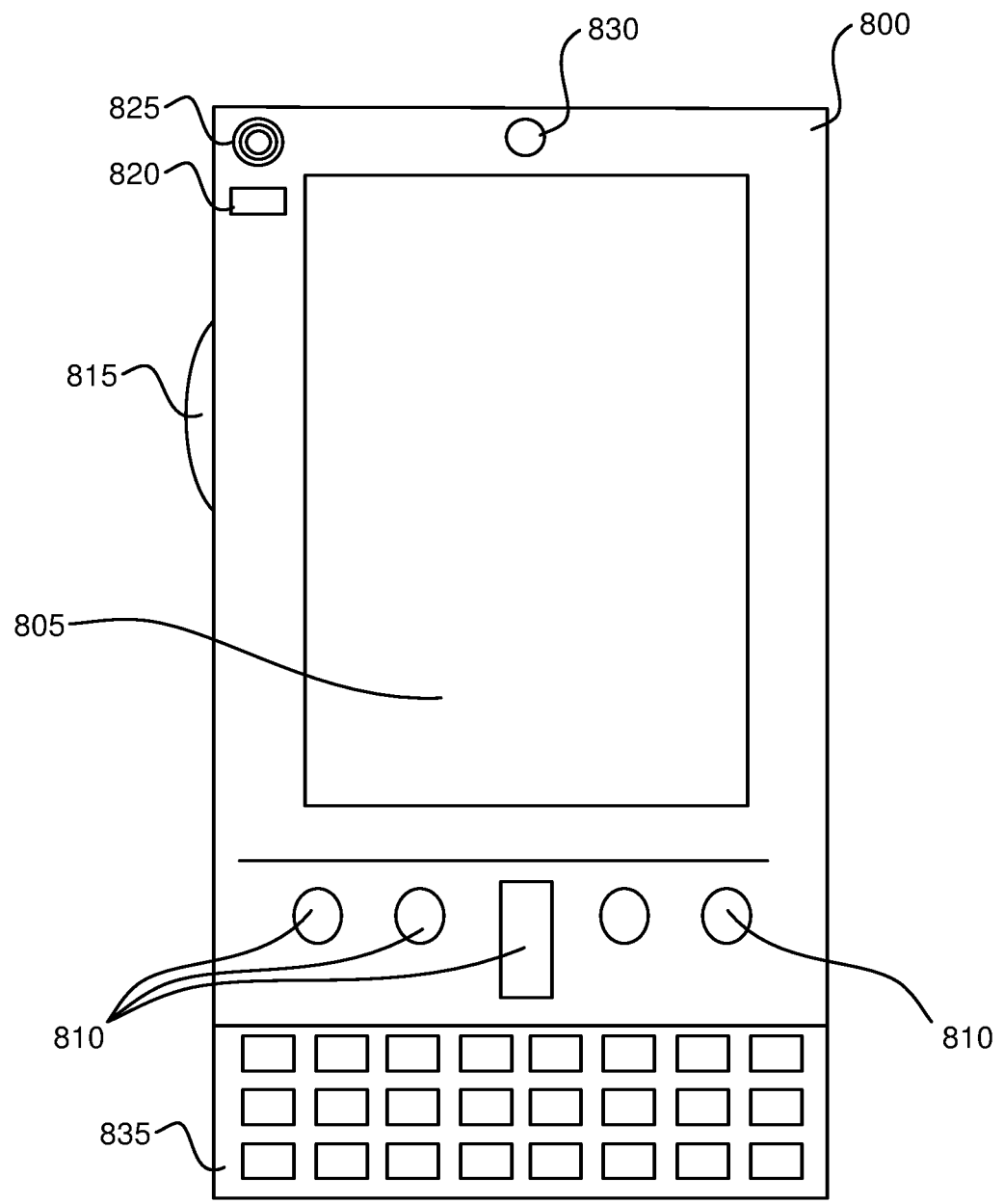
FIG. 8A is a simplified diagram of a mobile computing device with which aspects of the present disclosure may be practiced.
Figure 8B:
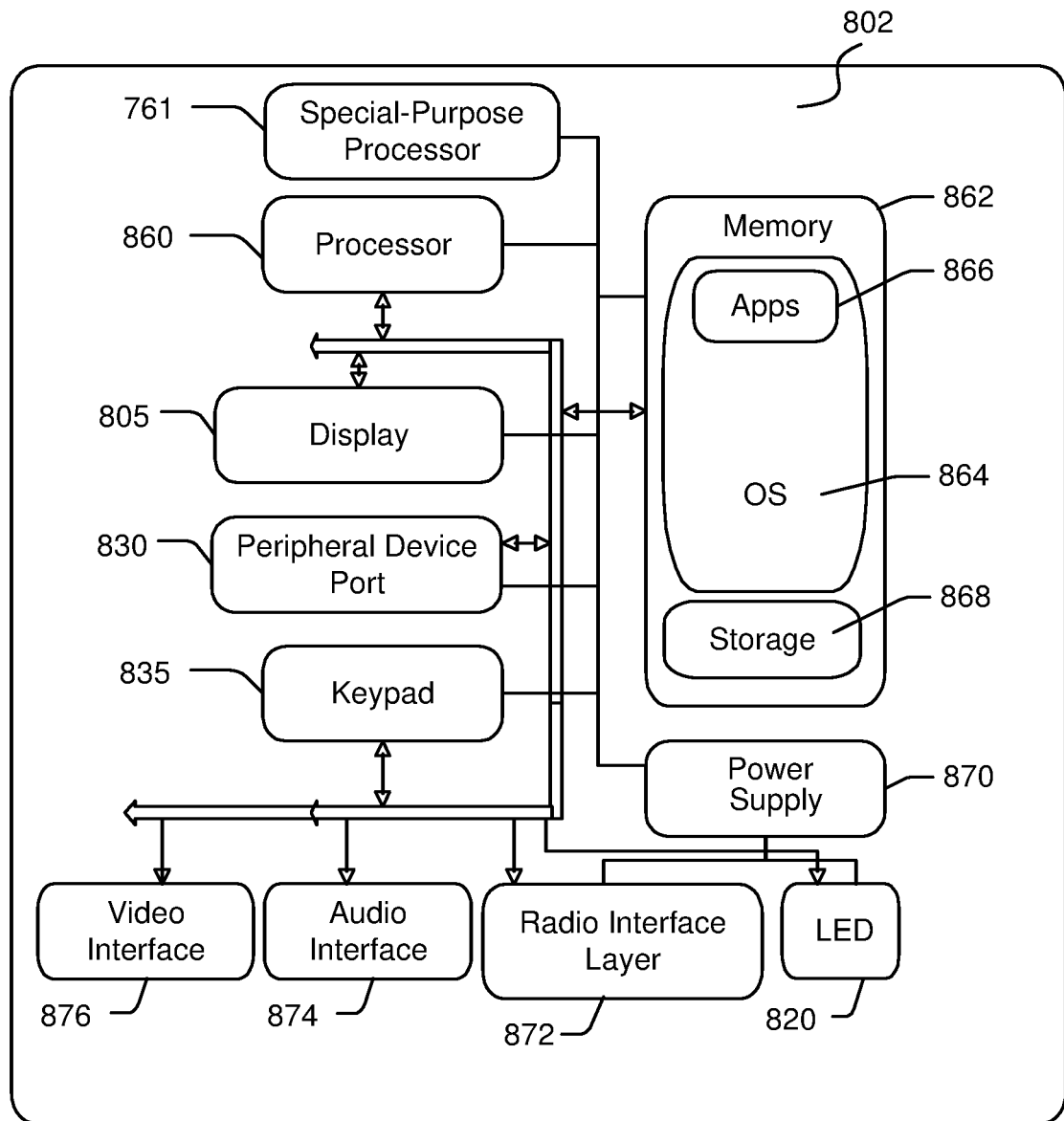
FIG. 8B is another simplified block diagram of a mobile computing device with which aspects of the present disclosure may be practiced.

FIGS. 8A and 8B illustrate a computing device or mobile computing device 800, for example, a mobile telephone, a smart phone, wearable computer (such as a smart watch), a tablet computer, a laptop computer, and the like, with which aspects of the disclosure may be practiced. In some aspects, the client utilized by a user (e.g., an operator of the system 100 in FIG. 1) may be a mobile computing device. With reference to FIG. 8A, one aspect of a mobile computing device 800 for implementing the aspects is illustrated. In a basic configuration, the mobile computing device 800 is a handheld computer having both input elements and output elements. The mobile computing device 800 typically includes a display 805 and one or more input buttons 810 that allow the user to enter information into the mobile computing device 800. The display 805 of the mobile computing device 800 may also function as an input device (e.g., a touch screen display). If included as an optional input element, a side input element 815 allows further user input. The side input element 815 may be a rotary switch, a button, or any other type of manual input element. In alternative aspects, mobile computing device 800 may incorporate more or less input elements. For example, the display 805 may not be a touch screen in some aspects. In yet another alternative aspect, the mobile computing device 800 is a portable phone system, such as a cellular phone. The mobile computing device 800 may also include an optional keypad 835. Optional keypad 835 may be a physical keypad or a "soft" keypad generated on the touch screen display. In various aspects, the output elements include the display 805 for showing a graphical user interface (GUI), a visual indicator 820 (e.g., a light emitting diode), and/or an audio transducer 825 (e.g., a speaker). In some aspects, the mobile computing device 800 incorporates a vibration transducer for providing the user with tactile feedback. In yet another aspect, the mobile computing device 800 incorporates input and/or output ports, such as an audio input (e.g., a microphone jack), an audio output (e.g., a headphone jack), and a video output (e.g., a HDMI port) for sending signals to or receiving signals from an external device.

FIG. 8B is a block diagram illustrating the architecture of one aspect of computing device, a server (e.g., the eye-gaze data collector 110 in FIG. 1), a mobile computing device, etc. That is, the mobile computing device 800 can incorporate a system 802 (e.g., a system architecture) to implement some aspects. The system 802 can implemented as a "smart phone" capable of running one or more applications (e.g., browser, e-mail, calendaring, contact managers, messaging clients, games, and media clients/players). In some aspects, the system 802 is integrated as a computing device, such as an integrated digital assistant (PDA) and wireless phone.

One or more application programs 866 may be loaded into the memory 862 and run on or in association with the operating system 864. Examples of the application programs include phone dialer programs, e-mail programs, information management (PIM) programs, word processing programs, spreadsheet programs, Internet browser programs, messaging programs, and so forth. The system 802 also includes a non-volatile storage area 868 within the memory 862. The non-volatile storage area 868 may be used to store persistent information that should not be lost if the system 802 is powered down. The application programs 866 may use and store information in the non-volatile storage area 868, such as e-mail or other messages used by an e-mail application, and the like. A synchronization application (not shown) also resides on the system 802 and is programmed to interact with a corresponding synchronization application resident on a host computer to keep the information stored in the non-volatile storage area 868 synchronized with corresponding information stored at the host computer. As should be appreciated, other applications may be loaded into the memory 862 and run on the mobile computing device 800 described herein.

The system 802 has a power supply 870, which may be implemented as one or more batteries. The power supply 870 might further include an external power source, such as an AC adapter or a powered docking cradle that supplements or recharges the batteries.

The system 802 may also include a radio interface layer 872 that performs the function of transmitting and receiving radio frequency communications. The radio interface layer 872 facilitates wireless connectivity between the system 802 and the "outside world," via a communications carrier or service provider. Transmissions to and from the radio interface layer 872 are conducted under control of the operating system 864. In other words, communications received by the radio interface layer 872 may be disseminated to the application programs 866 via the operating system 864, and vice versa.

The visual indicator 820 (e.g., LED) may be used to provide visual notifications, and/or an audio interface 874 may be used for producing audible notifications via the audio transducer 825. In the illustrated configuration, the visual indicator 820 is a light emitting diode (LED) and the audio transducer 825 is a speaker. These devices may be directly coupled to the power supply 870 so that when activated, they remain on for a duration dictated by the notification mechanism even though the processor 860 and other components might shut down for conserving battery power. The LED may be programmed to remain on indefinitely until the user takes action to indicate the powered-on status of the device. The audio interface 874 is used to provide audible signals to and receive audible signals from the user. For example, in addition to being coupled to the audio transducer 825, the audio interface 874 may also be coupled to a microphone to receive audible input, such as to facilitate a telephone conversation. In accordance with aspects of the present disclosure, the microphone may also serve as an audio sensor to facilitate control of notifications, as will be described below. The system 802 may further include a video interface 876 that enables an operation of an on-board camera 830 to record still images, video stream, and the like.

A mobile computing device 800 implementing the system 802 may have additional features or functionality. For example, the mobile computing device 800 may also include additional data storage devices (removable and/or non-removable) such as, magnetic disks, optical disks, or tape. Such additional storage is illustrated in FIG. 8B by the non-volatile storage area 868.

Data/information generated or captured by the mobile computing device 800 and stored via the system 802 may be stored locally on the mobile computing device 800, as described above, or the data may be stored on any number of storage media that may be accessed by the device via the radio interface layer 872 or via a wired connection between the mobile computing device 800 and a separate computing device associated with the mobile computing device 800, for example, a server computer in a distributed computing network, such as the Internet. As should be appreciated such data/information may be accessed via the mobile computing device 800 via the radio interface layer 872 or via a distributed computing network. Similarly, such data/information may be readily transferred between computing devices for storage and use according to well-known data/information transfer and storage means, including electronic mail and collaborative data/information sharing systems.

The description and illustration of one or more aspects provided in this application are not intended to limit or restrict the scope of the disclosure as claimed in any way. The aspects, examples, and details provided in this application are considered sufficient to convey possession and enable others to make and use the best mode of claimed disclosure. The claimed disclosure should not be construed as being limited to any aspect, for example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

The present disclosure relates to systems and methods for collecting eye-gaze data as training data for a gaze prediction model according to at least the examples provided in the sections below. The method comprises selecting a scan path from a set of predetermined scan paths, wherein each scan path is non-self-overlapping on a screen of a device, and wherein the scan path traverses across a series of regions in a grid on the screen; displaying a symbol as an eye-gaze target on the screen, wherein the symbol moves along the scan path for guiding attention of the operator; receiving a combination of eye-gaze point data and input images associated with a plurality of points along the scan path as training data for the eye-gaze prediction model, wherein the eye-gaze point data indicate a uniform distribution over the series of regions in the grid on the screen; training the eye-gaze prediction model using the training data, wherein the eye-gaze prediction model includes data associated with parameters in one or more neural networks; and updating the parameters in the one or more neural networks using the trained eye-gaze prediction model. A horizontal-vertical dimension ratio of each of the series of regions in the grid and a horizontal-vertical dimensional ratio of the screen are identical. Areas of one or more regions in the series of regions are identical. Areas of one or more regions in the series of regions adjacent to at least an edge of the screen are smaller than other regions in the series of the regions. The scan path passes through a point in a region of the series of regions, wherein the point represents an expected value of uniformly distributed random eye-gaze points in the region. The screen includes a plurality of screens, and wherein the scan path traverses across a series of regions in a grid on the plurality of screens. The method further comprising displaying the symbol without movement, wherein the symbol is on a scan path; selecting an icon from a set of icons, wherein the set of icons include an unrestricted movement of a face, a restricted movement of the face, and one or more actions, wherein the one or more actions include change distance, change position, change rotation, and change sides of a face of the operator; displaying the icon at a location adjacent to the symbol; and interactively receiving, in response to the displaying the icon, one or more input images of the operator.

Another aspect of the technology relates to a system for collecting eye-gaze data as training data for an eye-gaze prediction model. The system comprises a processor; and a memory storing computer-executable instructions that when executed by the processor cause the system to: select a scan path from a set of predetermined scan paths, wherein each scan path is non-self-overlapping on a screen of a device, and wherein the scan path traverses across a series of regions in a grid on the screen; display a symbol as an eye-gaze target on the screen, wherein the symbol moves along the scan path for guiding attention of the operator; receive a combination of eye-gaze data and input images associated with a plurality of points along the scan path as training data for the eye-gaze prediction model, wherein the eye-gaze point data indicate a uniform distribution over the series of regions in the grid on the screen; train the eye-gaze prediction model using the training data, wherein the eye-gaze prediction model includes data associated with parameters in one or more neural networks; and update the parameters in the one or more neural networks using the trained eye-gaze prediction model. A horizontal-vertical dimension ratio of each of the series of regions in the grid and a horizontal-vertical dimensional ratio of the screen are identical. Areas of one or more regions in the series of regions are identical. Areas of one or more regions in the series of regions adjacent to at least an edge of the screen are smaller than other regions in the series of the regions. The scan path passes through a point in a region of the series of regions, wherein the point represents an expected value of uniformly distributed random eye-gaze points in the region. The screen includes a plurality of screens, and wherein the scan path traverses across a series of regions in a grid on the plurality of screens. The computer-executable instructions that when executed by the processor further cause the system to: display the symbol without movement, wherein the symbol is on a scan path; select an icon from a set of icons, wherein the set of icons include an unrestricted movement of a face, a restricted movement of the face, and one or more actions, wherein the one or more actions include change distance, change position, change rotation, and change sides of a face of the operator; display the icon at a location adjacent to the symbol; and interactively receive, in response to the displaying the icon, one or more input images of the operator.

In still further aspects, the technology relates to a computer-readable recording medium storing computer-executable instructions. The computer-executable instructions that when executed by a processor cause a computer system to: select a scan path from a set of predetermined scan paths, wherein each scan path is non-self-overlapping on a screen of a device, and wherein the scan path traverses across a series of regions in a grid on the screen; display a symbol as an eye-gaze target on the screen, wherein the eye-gaze target moves along the scan path for guiding attention of the operator; receive a combination of eye-gaze data and input images associated with a plurality of points along the scan path as training data for the eye-gaze prediction model, wherein the eye-gaze point data indicate a uniform distribution over the series of regions in the grid on the screen; train the eye-gaze prediction model using the training data, wherein the eye-gaze prediction model includes data associated with parameters in one or more neural networks; and update the parameters in the one or more neural networks using the trained eye-gaze prediction model. A horizontal-vertical dimension ratio of each of the series of regions in the grid and a horizontal-vertical dimensional ratio of the screen are identical. Areas of one or more regions in the series of regions adjacent to at least an edge of the screen are smaller than other regions in the series of the regions. The scan path passes through a point in a region of the series of regions, wherein the point represents an expected value of uniformly distributed random eye-gaze points in the region. The screen includes a plurality of screens, and wherein the scan path traverses across a series of regions in a grid on the plurality of screens. The computer-executable instructions that when executed by the processor further cause the system to: display the symbol without movement, wherein the symbol is on a scan path; select an icon from a set of icons, wherein the set of icons include an unrestricted movement of a face, a restricted movement of the face, and one or more actions, wherein the one or more actions include change distance, change position, change rotation, and change sides of a face of the operator; display the icon at a location adjacent to the symbol; and interactively receive, in response to the displaying the icon, one or more input images of the operator.

Any of the one or more above aspects in combination with any other of the one or more aspect. Any of the one or more aspects as described herein.

What is claimed is:

1. A computer-implemented method for collecting eye-gaze data as training data for an eye-gaze prediction model, the method comprising:
   selecting a scan path from a set of predetermined scan paths, wherein each scan path is non-self-overlapping on a screen of a device, the scan path passes through a point in a region of a series of regions in a grid on the

17 screen, and the point represents an expected value of uniformly distributed random eye-gaze points in the region;

displaying a symbol as an eye-gaze target on the screen, wherein the eye-gaze target moves along the scan path for guiding attention of the operator;

receiving a combination of eye-gaze point data and input images associated with a plurality of points along the scan path as training data for the eye-gaze prediction model;

training the eye-gaze prediction model using the training data, wherein the eye-gaze prediction model includes data associated with parameters in one or more neural networks; and updating the parameters in the one or more neural networks using the trained eye-gaze prediction model.

2. The computer-implemented method of claim 1, wherein a horizontal-vertical dimension ratio of each of the series of regions in the grid and a horizontal-vertical dimensional ratio of the screen are identical.

3. The computer-implemented method of claim 1, wherein areas of one or more regions in the series of regions are identical.

4. The computer-implemented method of claim 1, wherein areas of one or more regions in the series of regions adjacent to at least an edge of the screen are smaller than other regions in the series of the regions.

5. The computer-implemented method of claim 1, wherein the screen includes a plurality of screens, and wherein the scan path traverses across a series of regions in a grid on the plurality of screens.

6. The computer-implemented method of claim 1, the method further comprising:

displaying the symbol without movement, wherein the symbol is on a scan path;

selecting an icon from a set of icons, wherein the set of icons include an unrestricted movement of a face, a restricted movement of the face, and one or more actions, wherein the one or more actions include change distance, change position, change rotation, and change sides of a face of the operator;

displaying the icon at a location adjacent to the symbol; and interactively receiving, in response to the displaying the icon, one or more input images of the operator.

7. A system for collecting eye-gaze data as training data for an eye-gaze prediction model, the system comprising:

a processor; and a memory storing computer-executable instructions that when executed by the processor cause the system to:

select a scan path from a set of predetermined scan paths, wherein each scan path is non-self-overlapping on a screen of a device, the scan path passes through a point in a region of a series of regions in a grid on the screen, and the point represents an expected value of uniformly distributed random eye-gaze pints in the region;

display a symbol as an eye-gaze target on the screen, wherein the eye-gaze target moves along the scan path for guiding attention of the operator;

receive a combination of eye-gaze data and input images associated with a plurality of points along the scan path as training data for the eye-gaze prediction model;

18 train the eye-gaze prediction model using the training data, wherein the eye-gaze prediction model includes data associated with parameters in one or more neural networks; and update the parameters in the one or more neural networks using the trained eye-gaze prediction model.

8. The system according to claim 7, wherein a horizontal-vertical dimension ratio of each of the series of regions in the grid and a horizontal-vertical dimensional ratio of the screen are identical.

9. The system according to claim 7, wherein areas of one or more regions in the series of regions are identical.

10. The system according to claim 7, wherein areas of one or more regions in the series of regions adjacent to at least an edge of the screen are smaller than other regions in the series of the regions.

11. The system according to claim 7, wherein the screen includes a plurality of screens, and wherein the scan path traverses across a series of regions in a grid on the plurality of screens.

12. The system according to claim 7, the computer-executable instructions that when executed by the processor further cause the system to:

display the symbol without movement, wherein the symbol is on a scan path;

select an icon from a set of icons, wherein the set of icons include an unrestricted movement of a face, a restricted movement of the face, and one or more actions, wherein the one or more actions include change distance, change position, change rotation, and change sides of a face of the operator;

display the icon at a location adjacent to the symbol; and interactively receive, in response to the displaying the icon, one or more input images of the operator.

13. A computer-readable recording medium storing computer-executable instructions that when executed by a processor cause a computer system to:

select a scan path from a set of predetermined scan paths, wherein each scan path is non-self-overlapping on a screen of a device, the scan path passes through a point in a region of a series of regions in a grid on the screen, and the point represents an expected value of uniformly distributed random eye-gaze points in the region;

display a symbol as an eye-gaze target on the screen, wherein the eye-gaze target moves along the scan path for guiding attention of the operator;

receive a combination of eye-gaze data and input images associated with a plurality of points along the scan path as training data for the eye-gaze prediction model;

train the eye-gaze prediction model using the training data, wherein the eye-gaze prediction model includes data associated with parameters in one or more neural networks; and update the parameters in the one or more neural networks using the trained eye-gaze prediction model.

14. The computer-readable non-transitory recording medium of claim 13, wherein a horizontal-vertical dimension ratio of each of the series of regions in the grid and a horizontal-vertical dimensional ratio of the screen are identical.

15. The computer-readable non-transitory recording medium of claim 13, wherein areas of one or more regions in the series of regions adjacent to at least an edge of the screen are smaller than other regions in the series of the regions.

16. The computer-readable non-transitory recording medium of claim 13, wherein the screen includes a plurality of screens, and wherein the scan path traverses across a series of regions in a grid on the plurality of screens.

17. The computer-readable non-transitory recording medium of claim 13, the computer-executable instructions that when executed by the processor further cause the system to:
- display the symbol without movement, wherein the symbol is on a scan path;
- select an icon from a set of icons, wherein the set of icons include an unrestricted movement of a face, a restricted movement of the face, and one or more actions, wherein the one or more actions include change distance, change position, change rotation, and change sides of a face of the operator;
- display the icon at a location adjacent to the symbol; and
- interactively receive, in response to the displaying the icon, one or more input images of the operator.

* * * * *